(12) United States Patent
Emara et al.

(10) Patent No.: US 11,206,997 B2
(45) Date of Patent: Dec. 28, 2021

(54) HANDBRAKE OF A MEDICAL IMAGING APPARATUS

(71) Applicant: Siemens Healthcare S.A.E., Cairo (EG)

(72) Inventors: Amr Emara, Cairo (EG); Hossam Mekky, Cairo (EG)

(73) Assignee: Siemens Healthcare S.A.E., Cairo (EG)

( * ) Notice: Subject to any disclaimer, the term of this patent is extended or adjusted under 35 U.S.C. 154(b) by 269 days.

(21) Appl. No.: 16/022,743

(22) Filed: Jun. 29, 2018

(65) Prior Publication Data
US 2020/0000365 A1    Jan. 2, 2020

(51) Int. Cl.
*A61B 5/055*      (2006.01)
*A61B 6/04*       (2006.01)
*A61B 6/10*       (2006.01)

(52) U.S. Cl.
CPC ............ *A61B 5/055* (2013.01); *A61B 6/0407* (2013.01); *A61B 6/105* (2013.01); *A61G 2210/50* (2013.01)

(58) Field of Classification Search
CPC ....... A47B 13/081; A61B 6/04; A61B 6/0407; A61B 6/0428; A61B 6/0421; A61B 5/704; A61B 5/70; A61B 5/0555; A61B 7/1042; A61B 7/1026; A61B 7/1034; A61B 5/055; A61B 6/105; Y10T 74/20774; A47C 21/04–048; A47C 21/006; F16D 2121/14; F16D 2129/04; F16D 2127/06; F16D 2125/18; F16D 63/00; F16D 63/006; A61G 2210/50; A61G 13/101; A61G 13/04; A61G 7/015; A61G 7/0528

USPC .............................................. 378/209; 5/601
See application file for complete search history.

(56) References Cited

U.S. PATENT DOCUMENTS

| | | | | |
|---|---|---|---|---|
| 2,567,566 A | * | 9/1951 | Kizaur | A61B 6/56 378/177 |
| 2,819,406 A | * | 1/1958 | Frecking, Jr. | G21K 1/025 378/204 |
| 3,428,307 A | * | 2/1969 | Hunter et al. | A47B 11/00 5/601 |
| 3,481,324 A | * | 12/1969 | Talbot | A61B 5/1102 600/527 |
| 4,130,070 A | * | 12/1978 | Herrin | A47B 13/081 108/143 |
| 5,596,779 A | * | 1/1997 | Meek | A61B 6/105 5/600 |

(Continued)

*Primary Examiner* — Eric J Kurilla
*Assistant Examiner* — Amanda L Bailey
(74) *Attorney, Agent, or Firm* — Schiff Hardin LLP (57) ABSTRACT

A handbrake of a medical imaging apparatus that has a movable patient table with a top face on which a patient lies, fastens and releases the patient table when actuated. The handbrake with a mounting face and a first face has a main body and has a brake actuation button, operable in an actuation direction. The mounting face is attachable to the patient table. The front face is directly opposite to at least some parts of the mounting face in the actuation direction. The brake actuation button is disposed on the front face of the main body, and is actuated by pushing the brake actuation button in the actuation direction, in order to fasten or to release the brake of the patient table. The actuation direction is essentially perpendicular to the top face of the patient table.

16 Claims, 4 Drawing Sheets

(56) References Cited

U.S. PATENT DOCUMENTS

| | | | | |
|---|---|---|---|---|
| 6,045,262 A | * | 4/2000 | Igeta | A61B 6/0487 |
| | | | | 378/209 |
| 7,874,030 B2 | * | 1/2011 | Cho | A61B 5/0555 |
| | | | | 5/601 |
| 2002/0129446 A1 | * | 9/2002 | Heinold | A61B 5/0555 |
| | | | | 5/601 |
| 2011/0120352 A1 | * | 5/2011 | Marallo | A47B 13/081 |
| | | | | 108/25 |
| 2015/0216444 A1 | * | 8/2015 | Uhlemann | G01R 33/307 |
| | | | | 600/415 |
| 2015/0327670 A1 | * | 11/2015 | Chen | A47B 13/088 |
| | | | | 74/502.2 |
| 2017/0312159 A1 | * | 11/2017 | Fliege | A61G 13/02 |

* cited by examiner

HANDBRAKE OF A MEDICAL IMAGING APPARATUS

BACKGROUND OF THE INVENTION

Field of the Invention

The invention relates to handbrakes of medical imaging apparatuses, especially for open magnetic resonance imaging (MRI) apparatuses.

Description of the Prior Art

Handbrakes for medical imaging apparatuses are known in the prior art. These handbrakes serve to fasten and to release the patient table of the imaging apparatus, in order to selectively allow the table to be moved to a desired position and then fixed in the desired position. The movement of the patient table can be achieved either by the usage of a motor or by moving the patient table manually. Especially in the case of the patient table being moved manually, the patient table has to be fixed by a handbrake in order to hold the patient table in the desired position, e.g., the position required during image acquisition. The handbrakes therefore release the patient table when activated and fasten the patient table when released. The known handbrakes of the prior art are thereby designed so as to project in a direction normal to the patient table. Thus, these handbrakes have the disadvantage of being in the way when the patient is trying to mount or dismount the patient table of the device. This circumstance causes a high risk of injury to the patient, and furthermore, a high risk to the handbrake of being damaged or broken.

SUMMARY OF THE INVENTION

An object of the present invention is to provide a handbrake that presents no risk, or only a low risk, of injury for the patient.

One aspect of the invention relates to a handbrake of a medical imaging apparatus, especially for an open MRI-device, wherein the medical imaging apparatus has a movable patient table, the movable patient table having a top face for a patient to lie on, and wherein the handbrake selectively fastens or releases the patient table when actuated. The handbrake has a main body and a brake actuation button that is operable in an actuation direction. The main body has a mounting face and a front face, the mounting face being designed to be attached to the patient table of the medical imaging apparatus. The main body is designed so that when the mounting face is so attached to the patient table, this causes the front face to be located directly opposite at least some parts of the mounting face in the actuation direction. The brake actuation button is disposed on the front face of the main body and is actuated by pushing the brake actuation button in the actuation direction, in order to fasten or to release the brake of the patient table, wherein the actuation direction is at least essentially perpendicular to the top face of the patient table.

The medical imaging apparatus can be, for instance, an x-ray apparatus, x-ray computed tomography apparatus, positron emission tomography apparatus, or an MRI scanner. The actuator assembly of the medical imaging apparatus is intended to fasten or to release the brake of the patient table of the medical imaging apparatus. For instance, the brake is fastened when the actuation button is pushed in the actuation direction. The brake therefore serves to secure the movable patient table in a desired position. This means that the handbrake is intended to hold the patient table in a certain desired position if fastened or, when released, to allow a movement of the patient table especially in a moving plane that is essentially parallel to the top face of the patient table. This movement of the patient table can be realized, for example, by the use of electronic devices such as motors or by manually moving the patient table. In case the medical imaging apparatus is a MRI device having a permanent magnet, the patient table of the medical imaging apparatus may often only be moved manually, in order to reduce noise. In embodiments, an operator will actuate the handbrake and, at the same time, move the patient table, e.g., with the operator's hand actuating the handbrake The mounting face of the main body of the handbrake is designed to be attached to the patient table of the medical imaging apparatus. In order to do so, the mounting face is designed to be directed toward the patient table. For example, the mounting face can be intended to directly or indirectly contact a part of the top face of the patient table in order to achieve a reliable mounting of the mounting face to the patient table. The top face of the patient table is that part of the patient table, or which is intended for the patient to lie on during the image acquisition. In other words, the top face of the patient table can have a normal that is parallel or essentially parallel to the vertical upward direction. "Essentially parallel" means that an angle of up to 20 degrees may exist between the essentially parallel directions. For instance, the mounting face can be attached to the top face of the frame of the patient table.

The front face of the main body of the handbrake is intended to face away from the patient table. In particular, the front face can face in a vertical direction or in a direction essentially parallel to the vertical direction when the handbrake is in a mounted stage. Alternatively or additionally, the front face can be the part of the handbrake that faces the operator of the handbrake. In order to realize a compact handbrake, the mounting face of the main body is located directly opposite to at least some parts of the front face. In this context, "directly opposite" means that the front face and the mounting face delimit the main body in the positive and negative actuation directions, especially in a cutting plane that contains the actuation direction, wherein the mounting face and the front face are both cut by this cutting plane. The maximum distance from the mounting face to the front face in the actuation direction can, for instance, be 7 cm or less.

The actuation button of the handbrake is placed on the front face of the main body and can be oriented, for example, to face the user/operator of the handbrake. In order to ease the pushing of the actuation button, the actuation button can have a substantially rectangular shape. To fasten and/or to release the handbrake, the actuation button needs to be pushed into the actuation direction. For instance, in order to release the brake the actuation button needs to be moved in the actuation direction and the brake is fastened when the actuation button is released. In an embodiment, the handbrake has a return mechanism in order to automatically push the actuation button in a direction reverse to the actuation direction. In other words, the return mechanism of the handbrake should be capable to automatically return the actuation button to the unpressed position and thus can automatically release or fasten the handbrake, respectively.

The actuation direction of the handbrake is the direction in which the button needs to be moved in order to fasten or to release the handbrake. In other words, the actuation direction is the direction directed from a rest position (not pushed) to an actuation position (button is pushed) of the handbrake. In an exemplary embodiment, the actuation button is in the rest position when the handbrake is fastened and is in the actuation position when released. The transmission of the actuation information to the actual actuation element or to a brake pad of the handbrake can be realized, for example, by the usage of electronic transmission elements or by using mechanical transmission devices. The actuation direction is at least essentially perpendicular to the top face of the patient table. "At least essentially perpendicular" means that the actuation direction is at least essentially parallel to the normal of the top face of the patient table, wherein "essentially parallel" means that an angle of up to 20°, in some embodiments up to 10° can exist between the essential parallel directions. In an exemplary embodiment, the actuation direction is essentially parallel to the vertical direction when the handbrake is mounted to the patient table. The invention is therefore capable of providing a handbrake with small dimensions in the actuation direction and in the direction normal to the patient table. These small dimensions ensure that the handbrake has little or no risk of injury for the patient, and additionally, the handbrake has a low or no risk of being damaged or broken when the patient is mounting or dismounting the patient table.

In an exemplary embodiment, the maximum distance from the mounting face to the furthest away point of the actuation button in the actuation direction is 9 cm or less, in useful embodiments 7 cm or less, or even 5 cm or less.

In another embodiment, the mounting face of the handbrake has a fixing assembly for immovably fixing the handbrake to the medical imaging apparatus, especially to the patient table of the medical imaging apparatus. The immovable fixing of the handbrake to the patient table of the medical imaging apparatus is extremely cost-efficient due to the fact that expensive mechanisms for fixing the handbrake are unnecessary. Immovably fixing means that the fixing assembly fixes the handbrake in a way that the handbrake cannot be moved translationally and rotationally relative to the patient table. Additionally or alternatively, other parts of the handbrake can also have such a fixing assembly. "Have/has" thereby means that the fixing assembly is contacting that part of the handbrake (e.g. the mounting face) or extends through that part of the handbrake. The fixing assembly can, for instance, be a force or a formfitting fixing assembly. For example, the fixing assembly can include screws, rivets, welding lines, or gluing lines.

In another embodiment, the main body has a cover section which overlaps a side of the patient table. The cover section therefore covers the side of the patient table, wherein the "side" of the patient table can be a part of the patient table that is oriented in a vertical direction. Additionally, the cover section can be dimensioned such that the cover section covers the gap between the movable patient table and the immobile patient table base. Thus, the cover section can increase the operational safety of the handbrake. In an exemplary embodiment, the main body is L-shaped, wherein a branch of the L forms that part of the main body having the front face and the mounting face and the other branch forms the cover section. Additionally or alternatively, the cover section and the main body can be in one piece. By doing so, a structurally robust and reliable cover section can be achieved.

In another embodiment, the average direction of the normal of the front face is substantially parallel to the actuation direction. By doing so, the manual movement of the patient table is eased when pushing the actuation button into the actuation direction. The average direction of the normal of the front face can be determined, for example, by averaging the normal of the entire surface of the front face.

In another embodiment, at least one of the front face and the actuation button is convex shaped. This reduces the probability of injuries of the patient and the operator of the handbrake and, such a shape also eases the manual movement of the patient table. This is due to the fact that a convex shaped front face and a convex shaped actuation button respectively fits easier into the operator's palm. A convex shape of the actuation button and the front face respectively can be achieved, for example, by a round or a rounded surface, wherein the rounded surface can have an average normal that is at least directed essentially parallel to the horizontal direction.

In another embodiment, at least one of the front face and the actuation button has edges that are being rounded. Additionally, the corners of the at least one of the front face and the actuation button can be rounded as well. Rounding the corners and/or the edges of the front face of the actuation button reduces the probability of injuries of the operator. Moreover, such a front face design causes a comfortable feeling when operating the handbrake. For example, the radius of the rounding can be between 2-9 mm, in order to avoid areas having a high local pressure in the operator's palm when engaging the handbrake.

In another embodiment, a projection of the front face onto a projection plane completely or at least almost completely encloses a projection of the brake actuation button onto the projection plane, wherein the actuation direction is parallel to a normal of the projection plane. Additionally, the direction of projection can also be parallel to the actuation direction. By doing so, the risk of accidently pushing the brake actuation button can be minimized and thus increases the operational safety of the handbrake and the medical imaging apparatus respectively. "Almost completely" in this context means that at least 75% of the outer contour of the projection of the brake actuation button is enclosed by the projection of the front face.

In another embodiment, the brake actuation button has a front side, wherein the front side has a normal parallel or essentially parallel to the average direction of the normal of the front face, wherein at least one, and advantageously all, of the edges of the front side is/are rounded. This makes the handbrake very ergonomic and thus eases the usage. The front side of the actuation button can be that side of the actuation button that is intended to face the operator. In other words, the front face of the actuation button can be that side of the actuation button that is intended to receive most of the force needed in order to actuate the button. The front side of the actuation button can, for instance, have a squared or rounded shape, such as an oval or circular shape. The front side of the actuation button can be flat or even, or alternately the front side can be rounded in order to have a convex shape. If the front side is not even or flat, the relevant normal of the front side is the averaged normal of the front side.

In another embodiment, the brake actuation button is only displaceable in a linear way. This simplifies the operation of the handbrake. Furthermore, this also eases the mounting of the actuation button. "Only displaceable in a linear way" means that the brake actuation button can only be moved in a translational direction and can thus not be moved in a rotational direction.

In another embodiment, at least one of the brake actuation button, the mounting face, and the front face are made of plastic. The usage of plastic insures a cheap handbrake. Additionally, plastic is capable of preventing corrosion, thus resulting in a long lifespan of the handbrake. Additionally a main body of the handbrake can be made out of plastic, wherein the main body contains the front face and the mounting face.

In another embodiment, the front face has a recess, wherein the actuation button is at least partly inserted into the recess when the actuation button is pushed in the actuation direction. By doing so, the risk of injury of the operator of the handbrake can be reduced. The recess can be designed in such a way that the front side of the actuation button is flush with the front face of the main body when the actuation button is pushed to the farthest position in the actuation direction. Due to this design, the possibility of injuries can be reduced even further. Additionally or alternatively, the actuation button, and the recess can be designed such that the actuation button is inserted in the recess even when being in the rest position. By doing so, the operation safety can be further increased.

In another embodiment of the handbrake, the handbrake has an actuating element that is engageable with a patient table base, wherein, during this engagement, the patient table is being immovably fixed relative to the table base. This offers a convenient and effective way to fasten the handbrake. The engagement can be done in a form- or force-fitting manner. The patient table base is that part of the medical imaging apparatus that is designed to hold the patient table. For instance, the patient table base can be immovably fixed to the ground or to the medical imaging apparatus, in order to insure a reliable support of the patient table.

Another aspect of the invention relates to a handbrake for a medical imaging apparatus, particularly for an open MRI-device, the medical imaging apparatus having a movable patient table, the movable patient table having a top face for a patient to lie on, wherein the handbrake fastens and/or releases the patient table when actuated, the handbrake having a main body and a brake actuation button, wherein the main body has a mounting face and a front face wherein the mounting face is designed to be attached to the patient table of the medical imaging apparatus, wherein the brake actuation button is disposed on the front face of the main body, wherein the brake actuation button can be actuated by pushing the brake actuation button in an actuation direction in order to fasten and/or to release the brake of the patient table, wherein a ratio of the maximum distance of the actuation button to the mounting face in the actuation direction to the minimal lateral extension of the main body in a direction perpendicular to the actuation direction is within a range of 0.3 to 0.75.

This design of the handbrake results in a very compact handbrake, thus resulting in a handbrake having no or very low risk of patient injury. The minimum lateral extension of the main body can, for instance, be the minimum lateral extension of the main body in a direction parallel to a length direction of the patient table or in a width direction of the patient table. The length direction of the patient table and the width direction of the patient table are the directions in which the length or the width of the patient table are determined. The maximum distance of the actuation button to the mounting face is determined in the direction of the actuation direction. Furthermore, this handbrake may also have any of the additional features described in relation to the first aspect of the invention. In order to achieve a handbrake that is very easy to operate, the ratio of the maximum distance of the actuation button to the mounting face in the actuation direction to the minimal lateral extension of the main body in a direction perpendicular to the actuation direction should be within a range of 0.45-0.6.

Another aspect of the invention relates to a medical imaging apparatus, having a handbrake according to one of the embodiments of a handbrake described. By doing so, the advantages of the handbrake can be incorporated into a medical imaging apparatus. This medical imaging apparatus can be, for example, an x-ray apparatus, a closed or open MRI scanner, or a CT medical imaging apparatus.

DESCRIPTION OF THE PREFERRED EMBODIMENTS

Figure 1:
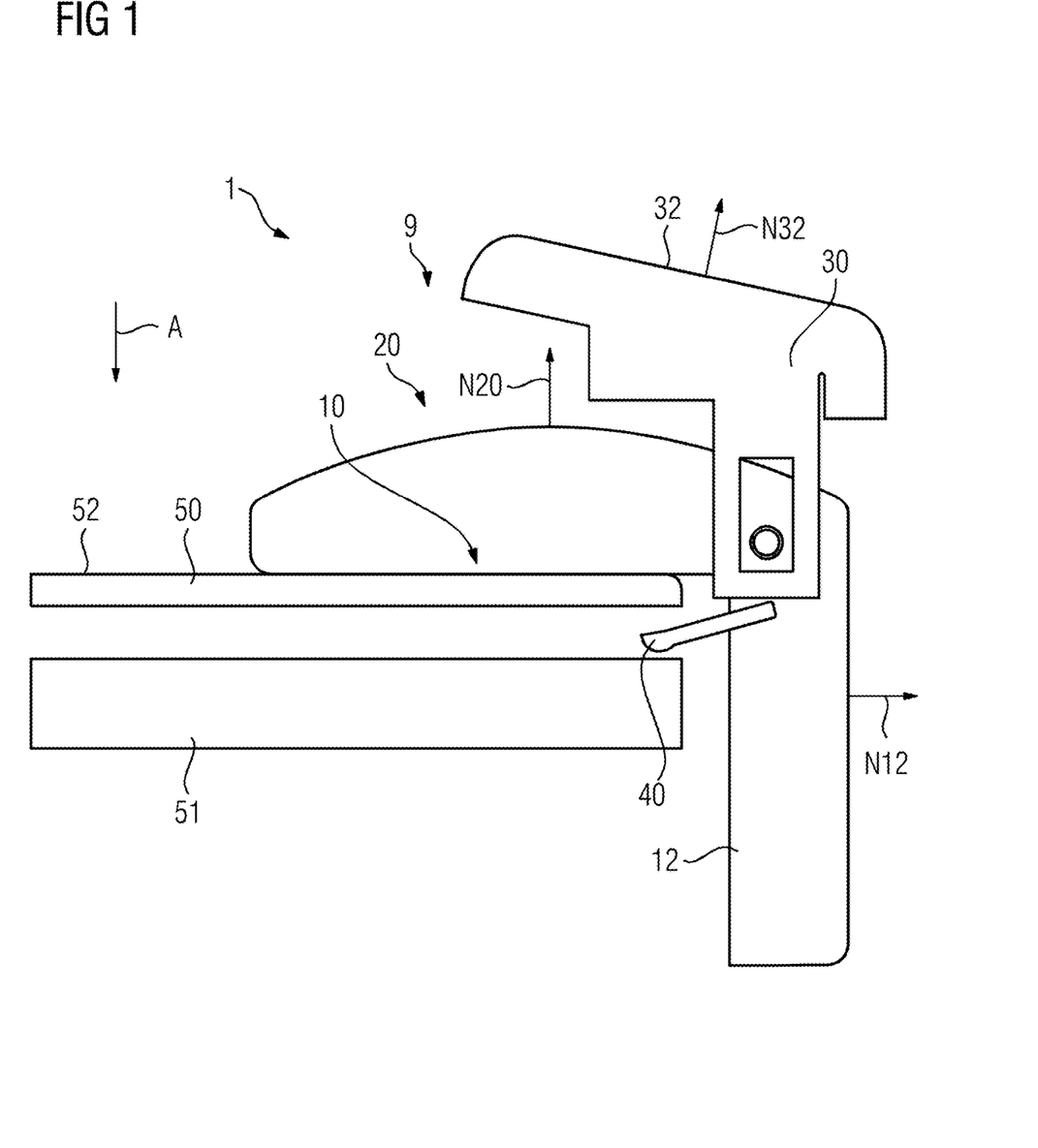
FIG. 1 is a sectional view of a handbrake according to the invention.

In FIG. 1, a sectional view a handbrake 1 is shown, wherein the handbrake 1 has a main body 9, having a mounting face 10, a front face 20, and a cover section 12. The main body 9 is made out of one piece and is L-shaped, wherein one branch of the L contains the front face 20 and the mounting face 10, and wherein the other branch of the L forms the cover section 12. The cover section 12 has an outward-pointing normal N12, and the cover section 12 covers the side of the patient table 50. The patient table 50 is fastened to the patient table base 51 by the transition element 40, serving as the brake or brake pad or brake actuator element. In the situation shown in FIG. 1, the handbrake 1 is fastened and thus, the patient table 50 is fixed. In order to release the handbrake 1, the brake actuation button 30, that is disposed on the front face 10 of the main body 9, needs to be pushed in the actuation direction A. This can for instance be done by applying a force to the front side 32 of the actuation button 30. In the situation shown in FIG. 1 the actuation direction A is parallel to the vertical direction. In order to prevent injuries the front face 32 has round edges. The outward-pointing normal N32 of the front side 32 is essentially parallel to the actuation direction A and to the average normal N20 of the front face 20. The front face 20 has a convex shape in order to ease the usability of the handbrake 1. Furthermore, the front face 20 has rounded edges on both edges delimiting the front face 20 in positive and negative direction of the normal N12 of the cover section 12. Directly opposite to the front face 20 in the actuation direction A, the main body 9 has a mounting face 10 that is directly contacting the patient table 50. The mounting face 10 has a planar shape that is parallel to some parts of the patent table 50, additionally, the mounting face has a fixing assembly (not shown) to immovably fix the handbrake 1 to the patient table 50.

Figure 2:
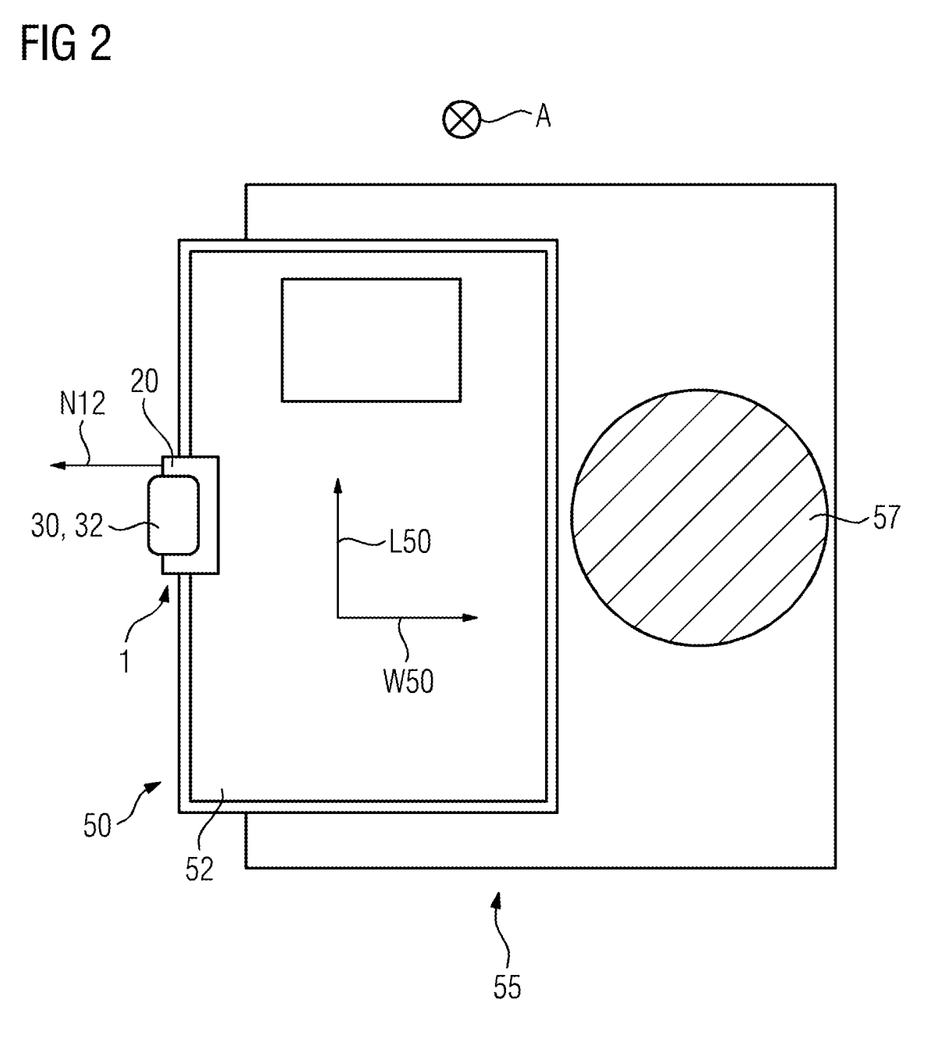
FIG. 2 is a schematic top view of a medical imaging apparatus according to the invention.

FIG. 2, a medical imaging apparatus 55 is illustrated, having an imaging region 57, a handbrake 1 and a patient table 50. The imaging region 57 of the medical imaging apparatus 55 can for instance have a magnet such as a permanent magnet or an electromagnet, if the medical imaging apparatus 55 is an MRI device. The patient table 50 has a top face 52 for a patient to lie on, wherein the patient is supposed to lie parallel to the length direction L50 of the patient table 50. The top face 52 of the patient table 50 lies within a plane that is being spanned by the length direction L50 of the patient table 50, and the width direction W50 of the patient table 50. The patient table 50 can for instance be moved in at least one of the length direction L50 and the width direction W50 of the patient table 50 respectively. The handbrake 1 is immovably fixed to the patient table 50 of the medical imaging apparatus 55 by a fixing assembly (not shown). The front face 20 of the main body 9 is facing in the actuation direction A. The actuation direction A is directed perpendicular to the length direction L50 of the patient table 50 and perpendicular to the width direction W50 of the patient table 50, and, additionally, perpendicular the normal N12 of the cover section 12. In order to release the handbrake 1, the actuation button 30 needs to be pushed in the actuation direction A. This can be done by applying a force to the front side 32 of the brake actuation button 30. In order to prevent injuries of the handbrake operator the front side 32 of the brake actuation button 30 has rounded corners and edges.

Figure 3:
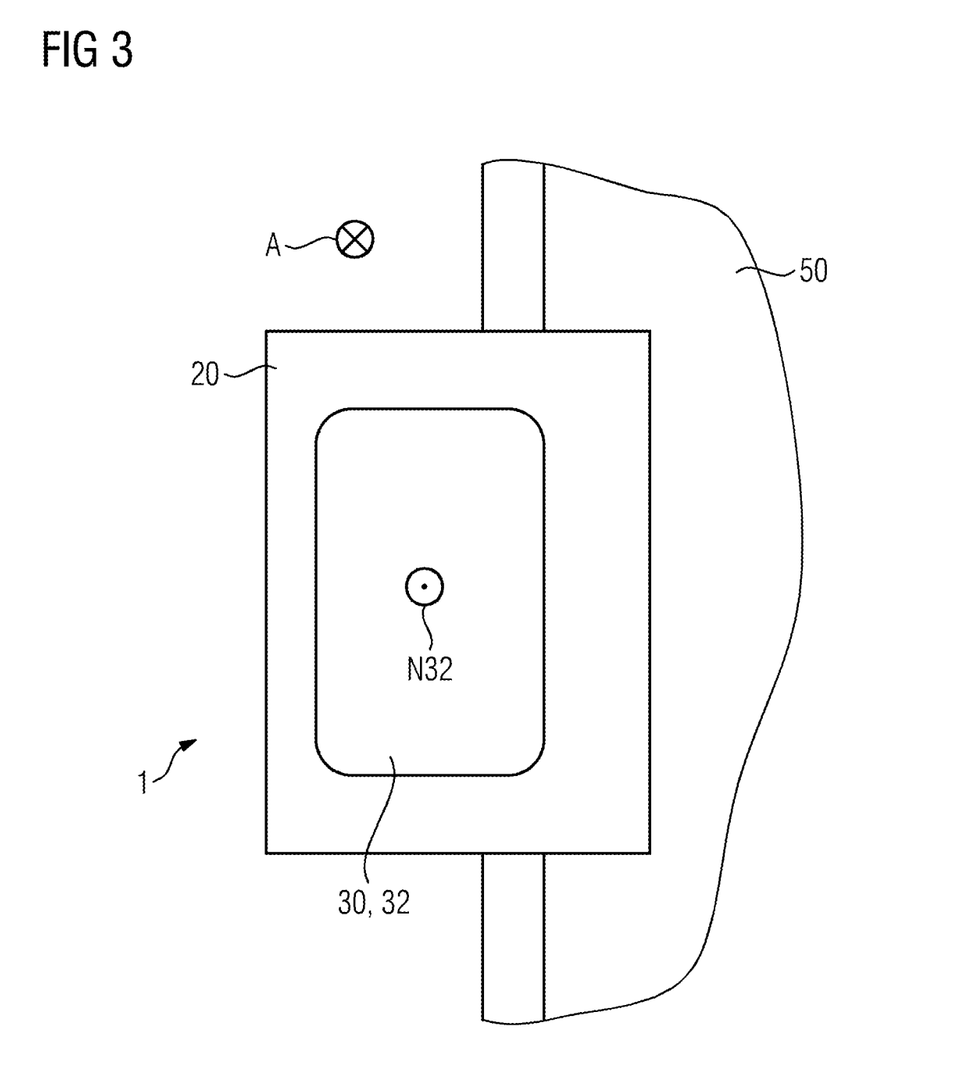
FIG. 3 is a top view of a handbrake according to the invention.

FIG. 3, another example of a handbrake 1 is illustrated. The handbrake 1 is having a front face 20, and a brake actuation button 30, wherein a projection of the front face 20 onto a projection plane, completely encloses a projection of the brake actuation button 30 on that projection plane, wherein the actuation direction A is parallel to a normal of the projection plane. The front face 20 is having sharp corners. On the other hand the front side 32 of the brake actuation button 30 is having rounded corners.

Figure 4:
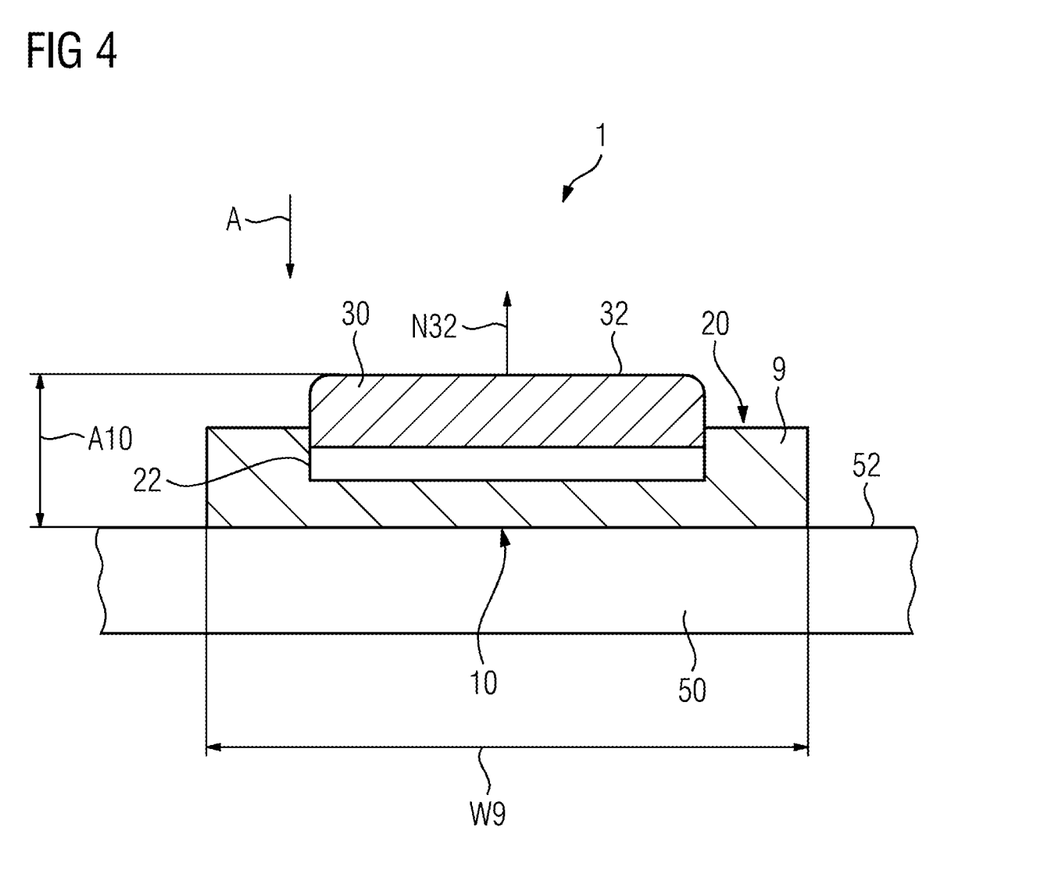
FIG. 4 is another schematic sectional view of a handbrake according to the invention.

FIG. 4 illustrates another sectional schematic view of a handbrake 1. The handbrake 1 is having an actuation button 30 that has a top face 32. The normal N32 of the top face 32 is parallel to the actuation direction A. The front face 20 of the main body 9 of the handbrake 1 has a recess 22, in which the actuation button 30 is at least partly contained. The mounting face 10 of the main body 9 of the handbrake 1 is directly contacting the top face 52 of the patient table 50. The ratio of the maximum distance A10 of the actuation button 30 to the mounting face 10 in the actuation direction A to the minimal lateral extension W9 of the main body 9 in a direction perpendicular to the actuation direction A, in the embodiment shown in FIG. 4, is approximately 0.4.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. Handbrake for a medical imaging apparatus having a moveable patient table, the movable patient table having a top face for a patient to lie on, the handbrake comprising:
    a main body and a brake actuation button, the handbrake being configured to fasten and/or release the patient table when actuated; and
    an actuating element that is configured to selectively engage a patient table base to fasten the movable patient table to the patient table base, the patient table being immovably fixed relative to the table base during engagement, wherein:
    the main body has a mounting face and a front face,
    the mounting face is configured to be attached to the patient table of the medical imaging apparatus,
    the front face is located directly opposite to at least some parts of the mounting face in a direction of an actuation direction,
    the brake actuation button is disposed on the front face of the main body,
    the brake actuation button is actuatable by pushing the brake actuation button in the actuation direction, in order to fasten and/or to release the brake of the patient table, the brake actuation button engaging the actuating element when pushed in the actuation direction to cause the actuating element to selectively engage the patient table base, and
    the actuation direction is at least essentially perpendicular to the top face of the patient table.

2. Handbrake according to claim 1, wherein the mounting face has a fixing assembly for immovably fixing the handbrake to the patient table of the medical imaging apparatus.

3. Handbrake according to claim 1, wherein the main body has a cover section, which overlaps a side of the patient table.

4. Handbrake according to claim 1, wherein the average direction of the normal of the front face is substantially parallel to the actuation direction.

5. Handbrake according to claim 1, wherein at least one of the front face and the actuation button is convex shaped.

6. Handbrake according to claim 1, wherein at least one of the front face and the actuation button has edges that are rounded.

7. Handbrake according to claim 1, wherein a projection of the front face onto a projection plane completely or at least almost completely encloses a projection of the brake actuation button onto the projection plane, wherein the actuation direction is parallel to a normal of the projection plane.

8. Handbrake according to claim 1, wherein:
    the brake actuation button has a front side,
    the front side has a normal parallel or essentially parallel to the average direction of the normal of the front face, and
    at least one of the edges of the front side is rounded.

9. Handbrake according to claim 1, wherein the brake actuation button is only linerally displaceable.

10. Handbrake according to claim 1, wherein the brake actuation button, the mounting face, and/or the front face are made of plastic.

11. Handbrake according to claim 1, wherein:
    the front face has a recess, and
    the actuation button is at least partly inserted into the recess, when the actuation button is being pushed in the actuation direction.

12. Handbrake for a medical imaging apparatus, the handbrake comprising:
    a main body, a brake actuation button, and an actuating element, wherein:
    the medical imaging apparatus has a moveable patient table, the movable patient table having a top face for a patient to lie on,
    the handbrake fastens and/or releases the patient table when actuated,
    the actuating element is configured to selectively engage a patient table base to fasten the movable patient table to the patient table base, the patient table being immovably fixed relative to the table base during engagement,
    the main body has a mounting face and a front face,
    the mounting face is designed to be attached to the patient table of the medical imaging apparatus,
    the brake actuation button is disposed on the front face of the main body,
    the brake actuation button is actuatable by pushing the brake actuation button in an actuation direction, in order to fasten and/or to release the brake of the patient table, the brake actuation button engaging the actuating element when pushed in the actuation direction to cause the actuating element to selectively engage the patient table base, a ratio of the maximum distance of the actuation button to the mounting face in the actuation direction to the minimal lateral extension of the main body in a direction perpendicular to the actuation direction is within a range of 0.3 to 0.75.

13. Handbrake according to claim 1, wherein a ratio of a maximum distance of the actuation button to the mounting face in the actuation direction to a minimal lateral extension of the main body in a direction perpendicular to the actuation direction is within a range of 0.3 to 0.75.

14. Handbrake according to claim 1, wherein the main body is L-shaped and the front face of the main body is convex shaped.

15. Handbrake according to claim 1, wherein the medical imaging apparatus is an open magnetic resonance imaging (MRI) device.

16. Handbrake according to claim 12, wherein the medical imaging apparatus is an open magnetic resonance imaging (MRI) device.

* * * * *